(12) United States Patent
Hollopeter et al.

(10) Patent No.: US 11,659,642 B1
(45) Date of Patent: May 23, 2023

(54) SURGICAL LIGHTING SYSTEM CO-ILLUMINATION DETECTION

(71) Applicant: American Sterilizer Company, Mentor, OH (US)

(72) Inventors: Michael Hollopeter, Kirtland, OH (US); Benjamin Yoder, University Heights, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 17/543,129

(22) Filed: Dec. 6, 2021

(51) Int. Cl.
| | |
|---|---|
| *H05B 47/11* | (2020.01) |
| *A61B 90/30* | (2016.01) |
| *A61B 90/35* | (2016.01) |
| *F21V 21/28* | (2006.01) |
| *F21W 131/205* | (2006.01) |
| *F21S 8/04* | (2006.01) |

(52) U.S. Cl.
CPC .............. *H05B 47/11* (2020.01); *A61B 90/30* (2016.02); *A61B 90/35* (2016.02); *F21S 8/046* (2013.01); *F21V 21/28* (2013.01); *F21W 2131/205* (2013.01)

(58) Field of Classification Search
CPC ...... H05B 45/10; H05B 47/10; H05B 47/105; H05B 47/11; A61B 90/35; F21S 8/046; F21V 21/28; F21W 2131/205
See application file for complete search history.

(56) References Cited

U.S. PATENT DOCUMENTS

| | | | |
|---|---|---|---|
| 5,068,767 A | 11/1991 | Koyama | |
| 6,513,962 B1 * | 2/2003 | Mayshack | F21V 7/0008 362/583 |
| 6,880,957 B2 | 4/2005 | Walters | |
| 10,226,593 B2 | 3/2019 | Wendt et al. | |
| 10,271,398 B2 | 4/2019 | Hollopeter et al. | |
| 10,295,164 B2 | 5/2019 | Liang et al. | |
| 10,652,973 B2 | 5/2020 | Akita et al. | |

(Continued)

FOREIGN PATENT DOCUMENTS

| | | |
|---|---|---|
| CN | 108253390 A | 7/2018 |
| CN | 109519805 A | 3/2019 |

(Continued)

OTHER PUBLICATIONS

International Search Report issued in corresponding International Application No. PCT/US2022/051369 dated Mar. 29, 2023.

(Continued)

*Primary Examiner* — Jimmy T Vu

(74) *Attorney, Agent, or Firm* — Kusner & Jaffe

(57) ABSTRACT

A device and method for operating a lighting system varies a characteristic of visible light emitted by a first lighthead according to a predefined profile, and fixes a characteristic of visible light emitted by a second lighthead. A light sensor configured to view a focal area of the second lighthead detects a characteristic of visible light on a target surface over a period of time, and the characteristic of the light detected by the light sensor over the period of time is compared to the characteristic of light defined in the predetermined profile. A mode of operation of the first and second lighthead is determined based on the comparison.

19 Claims, 5 Drawing Sheets

(56) References Cited

U.S. PATENT DOCUMENTS

| | | | |
|---|---|---|---|
| 11,153,953 B2 * | 10/2021 | Alexanderson | ..... F21V 23/0471 |
| 2004/0129860 A1 | 7/2004 | Thibaud et al. | |
| 2009/0261759 A1 | 10/2009 | Fornasiero | |
| 2017/0030573 A1 | 2/2017 | Alexanderson et al. | |
| 2018/0124892 A1 | 5/2018 | Hollopeter et al. | |
| 2019/0324253 A1 | 10/2019 | Zapata et al. | |
| 2020/0214788 A1 | 7/2020 | Hallack et al. | |

FOREIGN PATENT DOCUMENTS

| | | |
|---|---|---|
| DE | 102016105152 A1 | 9/2017 |
| WO | WO2020/053217 A1 | 3/2020 |

OTHER PUBLICATIONS

Written Opinion issued in corresponding International Application No. PCT/US2022/051369 dated Mar. 29, 2023.

\* cited by examiner

SURGICAL LIGHTING SYSTEM CO-ILLUMINATION DETECTION

FIELD OF THE INVENTION

The present invention relates generally to surgical lighting systems, and more particularly to detection of a co-illuminated state of surgical lightheads in a surgical lighting system and automatically adjusting light intensity based on detection of the co-illumination state.

BACKGROUND OF THE INVENTION

Surgical lightheads have been used in operating rooms to provide increased light to a specific area of the room. For example, a surgical lighthead can be positioned within an operating room and can provide increased light to a specific area of a person being operated on within the operating room.

Co-illuminating a surgical wound via multiple lightheads is an often-used technique to minimize loss of illuminance due to unintentional light blockage (e.g., the head, shoulders, hands of surgical staff can sometimes block the light). Unintended consequences of such blockage are not well understood and can present non-optimal environmental conditions to the surgical staff. For example, the surgeon may be subjected to excessive heat that necessitates cooling of the operating room outside of Joint Commission recommendations. The excessive light output may also result in non-optimum viewing or eye fatigue, and also may subject the patient to increased radiation exposure over extended procedural periods, which can result in tissue burn or necrosis.

SUMMARY OF THE INVENTION

In accordance with the invention, a characteristic of visible light emitted from one or more lightheads is varied with respect to time while the same characteristic of visible light emitted by at least one other lighthead is fixed. The varying characteristic of the emitted visible light, which is slowly varied so as to be imperceptible to the operating room staff (thus avoiding eye fatigue and distractions due to transitions between characteristics) is used to detect co-illumination by the two (or more) lightheads. In this manner, co-illumination operational mode(s) can be automatically enabled and matched to timing that is typical of surgical operation (minutes-hours). Further, based on the detected mode the light output by the lightheads can be adjusted to reduce long-term exposure to unnecessary radiation levels and/or to address light blockage.

According to one aspect of the invention, a method is provided for operating a lighting system having a first lighthead and a second lighthead distinct from the first lighthead, the second lighthead having associated therewith a light sensor configured to detect an intensity of visible light incident on the target surface in the region where the second lighthead is focused. The method includes: varying a characteristic of visible light emitted by the first lighthead according to a predefined profile; fixing a characteristic of visible light emitted by the second lighthead; detecting by the light sensor a characteristic of visible light incident on the target surface over a period of time; comparing the characteristic of the light detected by the light sensor over the period of time to the characteristic of light defined in the predetermined profile; and determining if the first and second lighthead are operating in a co-illumination state or an independent based on the comparison.

In one embodiment, the method includes setting a mode of operation of the first and second lighthead based on the determined operating state.

In one embodiment, setting includes setting the mode of operation of the first and second lighthead to co-illumination mode when the comparison indicates the characteristic of the light detected by the light sensor is sufficiently well correlated with the characteristic of light defined by the predetermined profile.

In one embodiment, setting includes setting the mode of operation of the first and second lighthead to independent mode when the comparison indicates the characteristic of the light detected by the light sensor is substantially non-varying.

In one embodiment, the method includes upon setting co-illumination mode of operation, ramping an intensity of light emitted by the first and second lightheads down such that a combined light intensity produced by the first and second lightheads is at a predetermined intensity.

In one embodiment, the predetermined profile comprises a characteristic of light that has a sinusoidal profile.

In one embodiment, the predetermined profile has a characteristic of light that varies in frequency.

In one embodiment, the predetermined profile has a frequency less than 1 Hertz.

In one embodiment, the characteristic comprises an intensity of light.

In one embodiment, the characteristic is an intensity of light, and varying includes varying a peak-to-peak intensity of light by about 30 percent relative to a nominal intensity.

According to another aspect of the invention, a surgical lighting system includes: a first lighthead configured to selectively emit a first visible light in a first direction; a second lighthead distinct from the first lighthead, the second lighthead configured to selectively emit a second visible light in a second direction; a sensor corresponding to the second lighthead and configured to sense visible light in a focal area of the second lighthead; and a controller operatively coupled to the first lighthead, the second lighthead, and the sensor, the controller configured to vary a characteristic of the first visible light over a period of time according to a predefined profile, fix a characteristic of the second visible light over the period of time, and compare a characteristic of the light detected by the light sensor over the predetermined time to a characteristic of light in the predetermined profile; and determine if the first and second lighthead are operating in a co-illumination state or an independent state based on the comparison.

In one embodiment, the controller is configured to set a mode of operation of the first and second lighthead based on the determined operating state.

In one embodiment, the controller is configured to set the mode of operation of the first and second lighthead to co-illumination mode when the comparison indicates the characteristic of the light detected by the light sensor is sufficiently well correlated with the characteristic of light in the predetermined profile.

In one embodiment, the controller is configured to set the mode of operation of the first and second lighthead to independent mode when the comparison indicates the characteristic of the light detected by the light sensor is substantially non-varying.

In one embodiment, the controller, upon setting co-illumination mode, is configured to ramp an intensity of light emitted by the first and second lightheads down such that a combined light intensity produced by the first and second lightheads is at a predetermined intensity.

In one embodiment, the predetermined profile is a sinusoidal profile.

In one embodiment, the predetermined profile varies a frequency of a characteristic of the emitted light.

In one embodiment, a frequency of the predetermined profile is less than 1 Hertz.

In one embodiment, a peak-to-peak intensity of light set by the predetermined profile varies by up to about 30 percent relative to a nominal intensity.

An advantage of a device and method in accordance with the invention is that co-illumination detection can be implemented using existing smart operating room lighting system architecture, without the need for advanced digital signal processing, high-speed synchronous architecture or secondary emissions. As a result, significant cost savings can be realized. Further, non-optimum lighting conditions can be automatically alleviated through increasing (for shadow control) or decreasing (for limitation of energy) light output between multiple lightheads.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
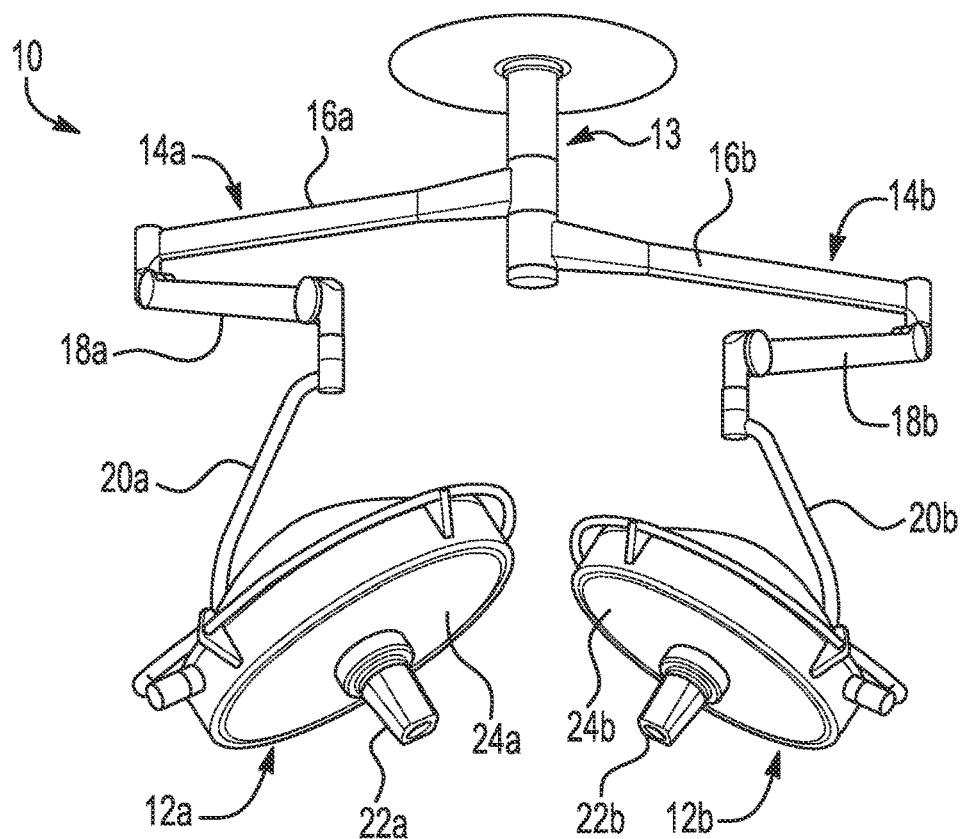
FIG. 1 is a perspective view of an exemplary surgical light to which aspects of the invention may be applied.

Aspects of the present invention will now be described with reference to the drawings, wherein like reference numerals are used to refer to like elements throughout. Such aspects may be embodied in many different forms and should not be construed as limited to the embodiments set forth herein; rather, these embodiments are provided so that this disclosure will be thorough and complete, and will fully convey its scope to those skilled in the art. In particular, the present invention will be described in the context of a surgical lighting system used in an operating room. However, such description is intended to be exemplary, and those having ordinary skill in the art will appreciate that aspects of the present invention may be applied to other types of lighting systems. Further, it will be understood that the figures are not necessarily to scale.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

Referring to FIG. 1, illustrated is an exemplary surgical light 10 to which aspects of the present invention may be applied. The surgical light 10 is configured to be positioned within a room (e.g., operating room) and to provide increased light to a specific area of the room. While the surgical light 10 can be placed within an operating room, the surgical light 10 can also be placed in any area wherein increased light at a targeted location is desired. The surgical light 10 includes a plurality of lightheads 12a, 12b for emitting light on a target surface, each lighthead 12a, 12b being connected to a common hub 13 by arms 14a, 14b. Although two lightheads are illustrated, it will be appreciated that aspects of the invention are applicable to lighting systems with more than two lightheads. Also, other configurations of the surgical light are possible, including wall mount, floor mount, a movable support structure, etc.

In the illustrated example, the arms 14a, 14b of the surgical light 10 allow light from the respective lightheads 12a, 12b to be pointed or concentrated at a certain area within the operating room (with the suspension system allowing the respective lighthead 12a, 12b to be selectively positioned within the operating room). The arms 14a, 14b include a first arm member 16a, 16b configured to be rotatably connected to the hub 13, a second arm member 18a, 18b rotatably connected to the respective first arm member 16a, 16b, and a curved link 20a, 20b extending between the second arm member 18a, 18b and the lighthead 12a, 12b. The first arm members 16a, 16b, the second arm members 18a, 18b and the curved links 20a, 20b allow the lightheads 12a, 12b to be moved to any desired location by grasping a handle assembly 22a, 22b extending from a circular face plate 24a, 24b of the respective lighthead 12a, 12b and pulling, pushing and/or twisting the lighthead 12a, 12b to any desired location. While a specific arm 14a, 14b is illustrated in FIG. 1, any arm well known to those skilled in the art could be used to connect the lightheads 12a, 12b to the operating room structure or a movable assembly as discussed above (including one connected to multiple points on the side of the lighthead 12a, 12b and/or the rear surface thereof). The illustrated arms 14a, 14b or any arm known to those skilled in the art allows for easy movement of the light assemblies 12a, 12b into any position within the operating room and then maintaining the position of the lightheads 12a, 12b once released.

Figure 2:
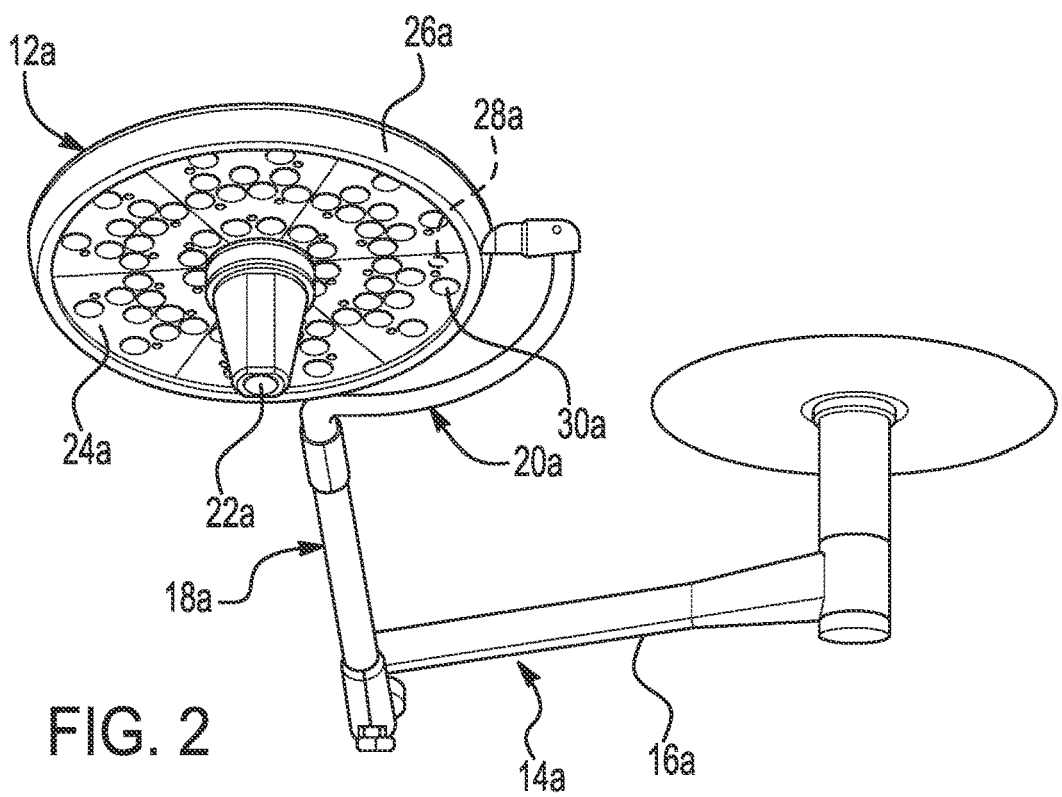
FIG. 2 is a detailed view of one lighthead of the surgical light of FIG. 1.

With additional reference to FIG. 2, illustrated is one lighthead 12a of FIG. 1 in more detail. As will be appreciated, the features shown in FIG. 2 may be duplicated for the second lighthead 12b. The illustrated lighthead 12a includes a respective housing 26a having at least one light emitting assembly 28a contained therein. Each light emitting assembly 28a includes a light source (e.g., an LED or a plurality of LEDs) covered by light directing optics 30a. The housing 26a includes the circular face plate 24a covering the at least one light emitting assembly 28a, with the handle assembly 22a for moving the lighthead 12a extending from the center of the circular face plate 24a. The handle assembly 22a can also be used for turning on, turning off, or increasing and decreasing, for example, the intensity, spot size or color of the light emitted by the light emitting assembly 28a within the lighthead 12a. Housings for light assemblies and the light sources and optics therein are well known to those skilled in the art. For example, the housing, light source and optics can be those of U.S. Patent Application Publication No. 2014/0268751 entitled SURGICAL LIGHT WITH BEAM REDIRECTING OPTICS, the entire contents of which are incorporated herein by reference. A specific design and construction of lightheads 12a and 12b are illustrated in FIG. 1 and FIG. 2, however one skilled in the art could contemplate many other suitable lighthead shapes and constructions that are capable of varying the intensity of the light emitted and sensing the amount of light incident on the surgical site.

Figure 3A:
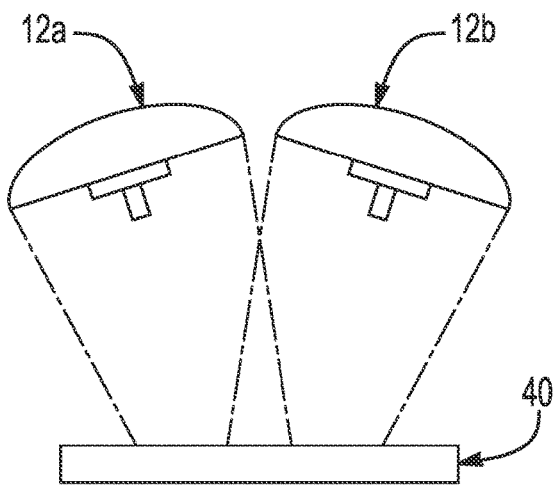
FIG. 3A is a side schematic view of the surgical light of FIG. 1 having a configuration in which there is at least partial overlap of focal areas of the respective light assemblies.
Figure 3B:
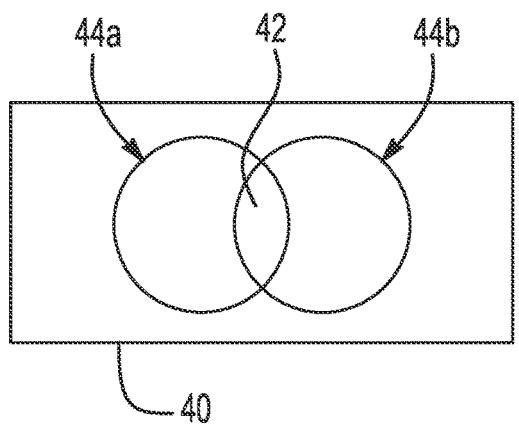
FIG. 3B is a top view illustrating the partial overlap of focal areas using the configuration of FIG. 3A.
Figure 4A:
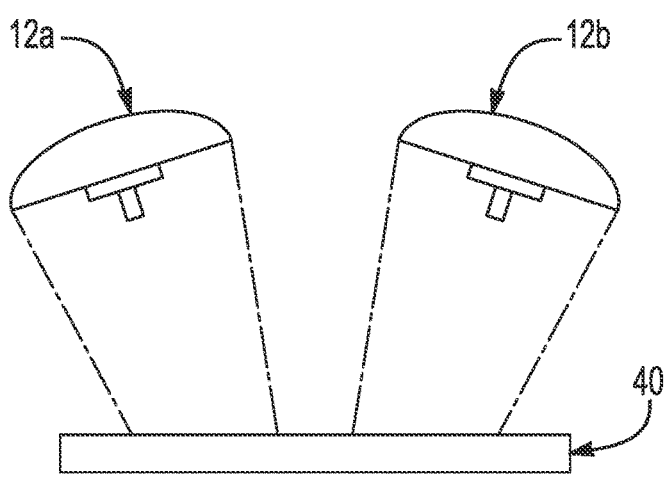
FIG. 4A is a side schematic view of the surgical light of FIG. 1 having a configuration in which there is no overlap of focal areas of the respective light assemblies.
Figure 4B:
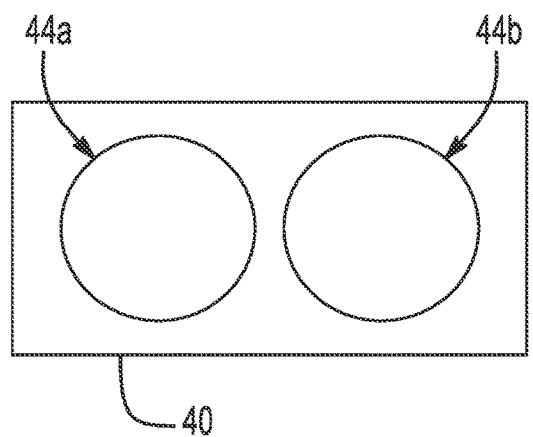
FIG. 4B is a top view illustrating no overlap of focal areas using the configuration of FIG. 4A.

Moving now to FIGS. 3 and 4, illustrated are two exemplary configurations of the lightheads 12a, 12b. In FIG. 3 lighthead 12a and lighthead 12b emit light in the same direction onto an object 40. As illustrated, there is an area of overlap 42 of the focal area 44a from the first lighthead 12a and the focal area 44b from the second lighthead 12b (i.e., co-illumination). While a partial overlap is shown in FIG. 3, the light assemblies could be adjusted to vary the region of overlap such that all or substantially all of the focal area 44a and 44b overlap with each other. In contrast to FIG. 3, FIG. 4 illustrates a configuration of the light assemblies 12a, 12b in which the focal areas 44a and 44b do not overlap with each other.

As discussed above, it is desirable to limit exposure to light energy in the operating room, as such exposure can generate excessive heat that requires cooling of the operating room, non-optimum viewing or eye fatigue for medical staff in the operating room, and increased radiation exposure for patients and medical staff over extended procedural exposures. A device and method in accordance with the invention can reduce exposure to light energy. More particularly, the occurrence of co-illumination of two or more lightheads is detected and, once detected, steps are taken to reduce the light energy output by the lightheads 12a, 12b. The device and method in accordance with the invention can detect such co-illumination without use of a secondary emission technology. In other words, in accordance with the invention co-illumination is detected based on visible light emitted by the respective lightheads 12a, 12b in a manner that is imperceptible to medical personnel in the presence of the lightheads 12a, 12b.

Figure 5:
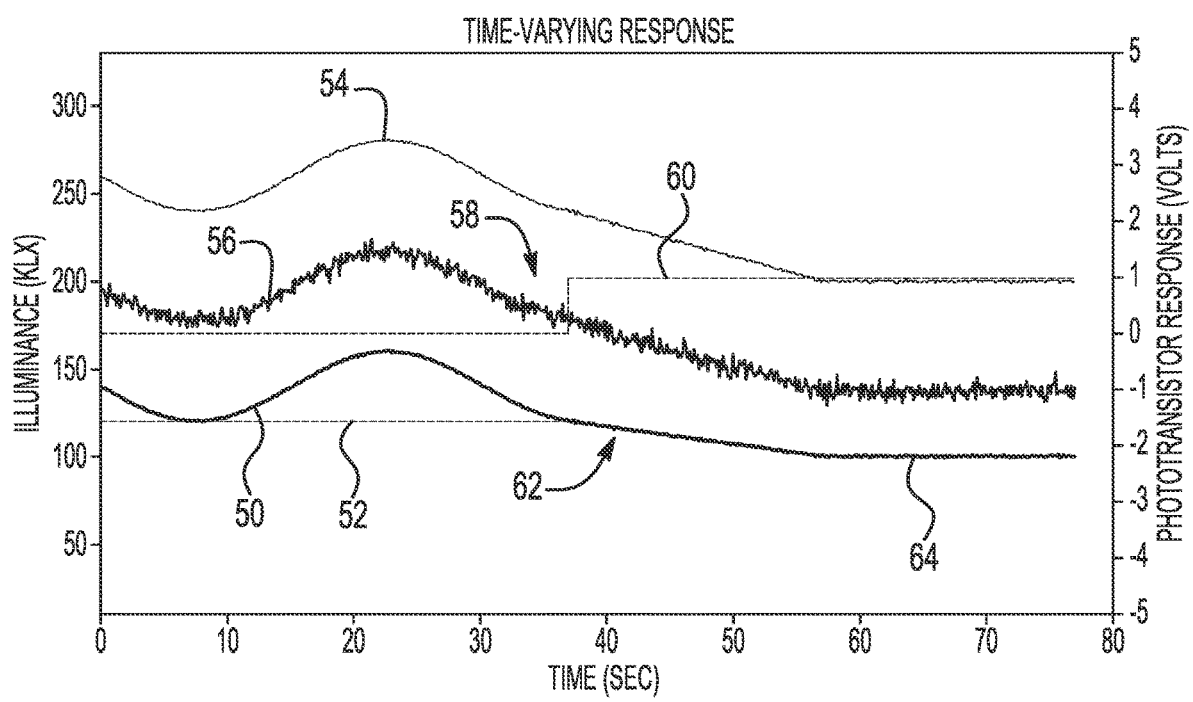
FIGS. 5 and 6 are graphs illustrating light output from each lighthead for both co-illumination mode (FIG. 5) and independent mode (FIG. 6) in accordance with an embodiment of the invention.

In accordance with the invention, and with reference to FIG. 5, a characteristic of visible light emitted by the first lighthead 12a is varied, for example, based on a predetermined profile 50, while a characteristic of visible light emitted by the second lighthead 12b is fixed 52 (i.e., the characteristic is maintained constant and does not significantly vary over time). The predetermined profile 50 may be any desired profile in which a characteristic of the light varies over time between two or more parameters. In the illustrated embodiment the predetermined profile is a sinusoidal profile, but other profiles are contemplated. The predetermined (e.g., sinusoidal) profile 50 can best be seen in FIG. 5 where between 0 and 35 seconds an intensity of light emitted by the first lighthead 12a is varied over time between a maximum value and a minimum value. The fixed output can be seen during the same 0-35 second window, wherein an intensity of light emitted by the second lighthead 12b is constant/fixed. Additionally or alternatively, a characteristic of the emitted light may be frequency dependent, where a frequency of oscillation between one complete cycle (i.e., between the two parameters) can be varied to provide an additional means for defining the profile.

Figure 6:
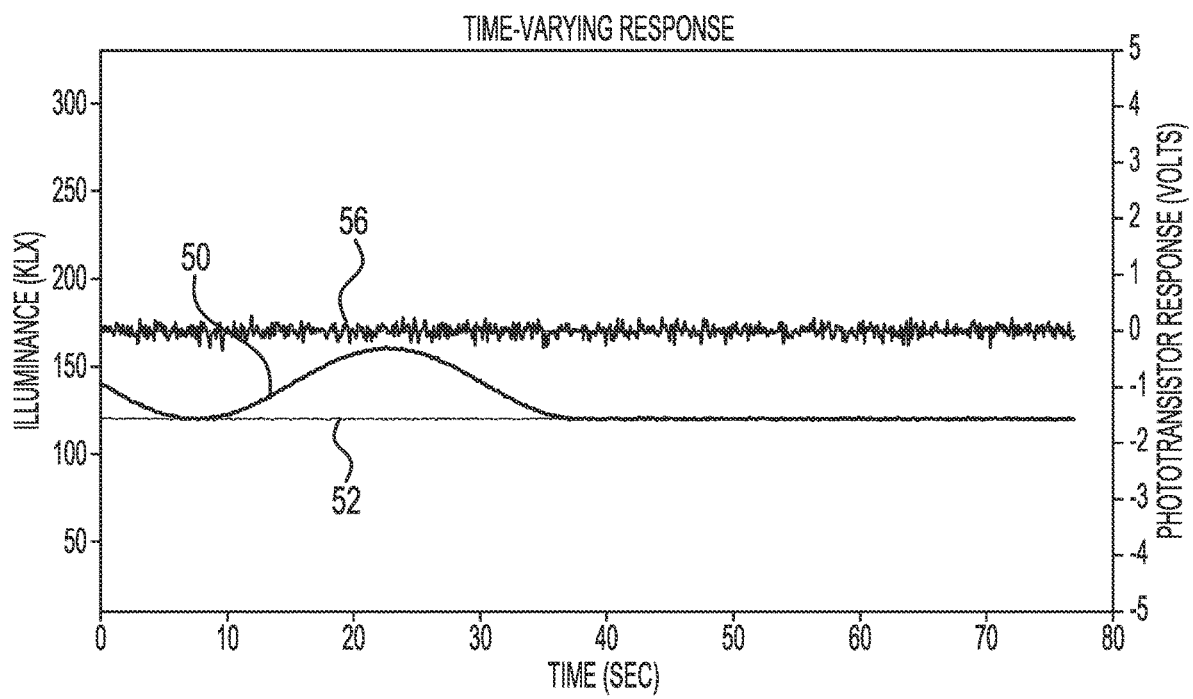

If co-illumination is occurring, then the light in the area of overlap 42 (FIG. 3) will be the sum of the portions of the light output by the first and second lightheads 12a, 12b, that is incident upon area of overlap 42, which in FIG. 5 is shown by the sinusoidal waveform 54. A light sensor (discussed below with respect to FIG. 7) associated with the lighthead having the fixed characteristic (e.g., the second lighthead 12b in the present example) monitors, over the period of time, the focal region 44b of the lighthead 12b and produces a signal 56 corresponding to the detected visible light. This monitored signal 56 is then subjected to a variety of signal processing techniques in order to prepare it for comparison with the lighthead 12a commanded light intensity profile 50 or the combined commanded intensity profile from both lightheads 54. Examples of general classes of signal processing techniques that can be applied include filtering, convolution, and scaling operations, though one skilled in the art could contemplate others. A correlation coefficient between the monitored signal 56 after processing and the commanded profile 50 or 54 is then calculated and compared to a predetermined threshold in order to establish whether the first and second lightheads 12a and 12b are in a state of co-illumination. The value of the predetermined threshold can vary depending on how large an overlap area 42 relative to the individual focal areas 44a and 44b is deemed to be necessary to constitute a co-illuminated state. If co-illumination is not occurring, then the monitored signal 56 will be substantially constant as illustrated in FIG. 6. This is due to the fact that there is no overlap between the focal regions 44a and 44b and thus no summation of light from the two lightheads. Therefore, the sensor associated with the second lighthead 12b (which in the present example has a fixed/non-varying characteristic of light) will only see the fixed light output of the second lighthead 12b. Thus, if the monitored signal 56 is substantially constant it can be concluded co-illumination is not occurring.

The characteristic of the visible light, which can be a color of the visible light (e.g., a warmth of the light) or an intensity of the visible light, is varied such that it is imperceptible to persons in the presence of the lightheads (i.e., the change is not perceivable to the human eye). For example, the characteristic of the emitted light can be varied in intensity about a specified nominal intensity level and/or can be changed in color about a specified nominal color, where the change between minimum and maximum intensity and/or a change from one color to the other occurs at a very slow rate, preferably less than 1 Hertz and more preferably much less than 1 Hertz. For example, in FIG. 5 the frequency is about 0.03 Hertz. Further, the change in intensity and/or color of the emitted light can be relatively small, e.g., up to about ±20-30 percent of a specified nominal intensity/color. It will be appreciated by one skilled in the art that in many circumstances the intensity of the visible light emitted from the lighthead will be substantially proportional to the total visible flux emitted by the light sources in the lighthead as well as the resulting illuminance in the focal area of the lighthead. As such it should understood that where changes in the intensity of visible light are described herein, changes in light source flux or changes in focal area illuminance would also apply.

For example, if the monitored signal 56 is light intensity, the monitored signal can be said to correlate to a profile of the summed light 54 if the correlation coefficient calculated between the monitored signal 56 following signal processing operation and the profile of the summed light 54 over a predefined time period exceeds a predetermined threshold. If the monitored signal 56 corresponds to a summed color of light, then the monitored signal 56 can be said to correspond to the summed profile 54 if the color is within a preset percentage of the profile color over a predefined time period and/or if the frequency of one complete cycle of color change (e.g., a first color to a second color and back to the first color) of the monitored signal is within a percentage of the frequency of color change in the predetermined profile.

It should be noted that the predetermined time period can be any time period. At very short time periods, less than about 35 milliseconds for example, changes in light output will occur too quickly to be perceptible to the human eye. If the changes occur over intermediate time periods, such as between about 35 milliseconds and about 10 seconds, the changes may be perceptible to the user which could be desirable in some circumstances. However, in many circumstances it is preferable that the time period be sufficiently large such that changes in the light output are not perceived. In this regard, time periods of 15-30 seconds or more are preferred given the length of time of procedures and the nature of radiant heat transfer.

Based on the comparison of the actual (monitored) characteristic of light and the summed profile 54, a decision as to current co-illumination state of the first and second lightheads 12a, 12b can be made and mode of operation of said lightheads set to either co-illumination mode or to independent operation mode. In setting the operational mode, if the comparison indicates the characteristic of the light detected by the light sensor is sufficiently well correlated with the predetermined profile then the mode is set to co-illumination mode, while if the comparison indicates the characteristic of the light detected by the light sensor is substantially non-varying and/or there is insufficient correlation between the monitored signal and the profile then the mode is set to independent mode.

If the lightheads are in independent mode then, and as seen in FIG. 6, the profile is removed from the first lighthead 12a (at about 35 seconds in FIG. 6) and in its place a fixed output is provided to the first lighthead 12a, while the second lighthead, which is already in a fixed output mode, requires no change. The intensity of each lighthead 12a, 12b continues to be controlled solely based on user input. However, if during the predetermined time period the lightheads 12a, 12b are found to be in co-illumination mode as indicated at 58 in FIG. 5, then a flag 60 is set to indicate co-illumination mode and an intensity of light emitted by the first and second lightheads 12a, 12b is ramped down (at about 35 second to 58 seconds in FIG. 5) such that the combined light intensity produced by the first and second lightheads is at a predetermined lower intensity (at about 58 seconds up). This is seen in FIG. 5 where a ramp 62 is applied to the light output of each lighthead 12a, 12b until a lower steady state output 64 for each lighthead is achieved. In this manner, light energy exposure to the patient and medical personnel can be reduced.

Figure 7:
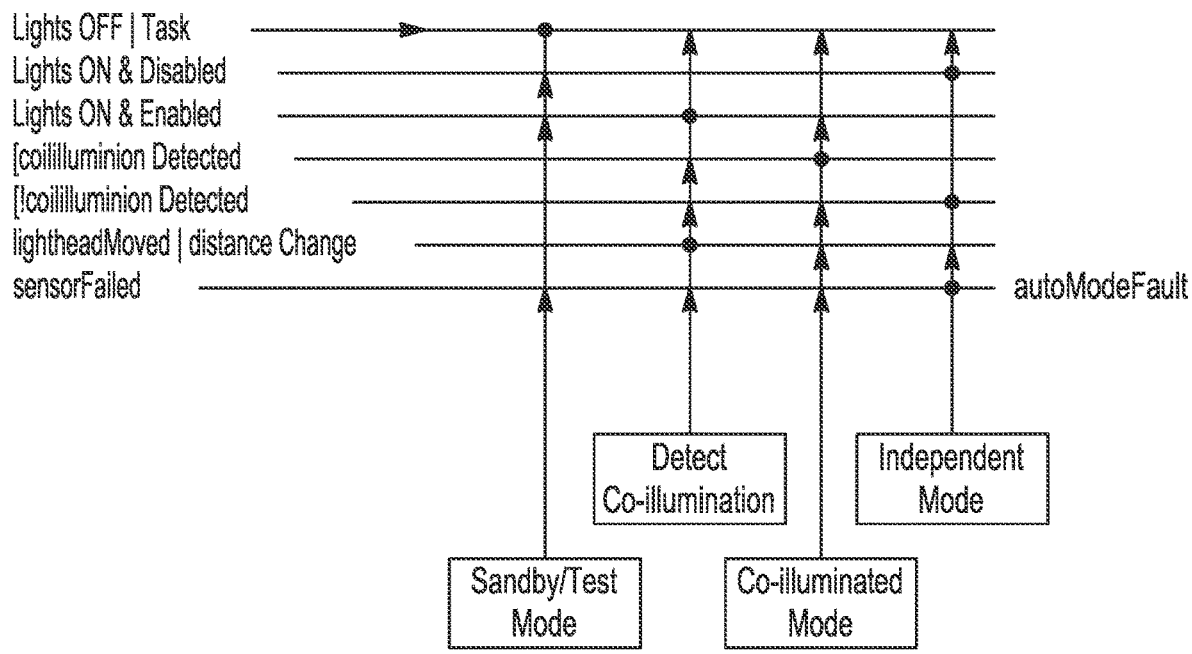
FIG. 7 is a state transition diagram illustrating various states of operation of the light system in accordance with the invention.

A state diagram of the lighting system in accordance with the invention is illustrated in FIG. 7. In the state diagram of FIG. 7, the current setting of the lighting system is shown on the upper-left of the figure and the state corresponding to the setting is shown on the lower-right of the figure. The state of the lighting system for the current setting is found by following the horizontal line adjacent to the respective setting to the right until a node connector is reached, and then dropping down along the line attached to the node connector to the box connected thereto. Thus, the states for each setting are as follows:

| | |
|---|---|
| Lights OFF → | Standby/test mode |
| Lights ON and disabled → | Independent mode |
| Lights ON and enabled → | Detect co-illumination |
| Co-illumination detected → | Co-illumination mode |
| Co-illumination not detected → | Independent mode |
| Lighthead moved/distance changed → | Detect co-illumination |
| Sensor failed → | Auto mode fault |

Figure 8:
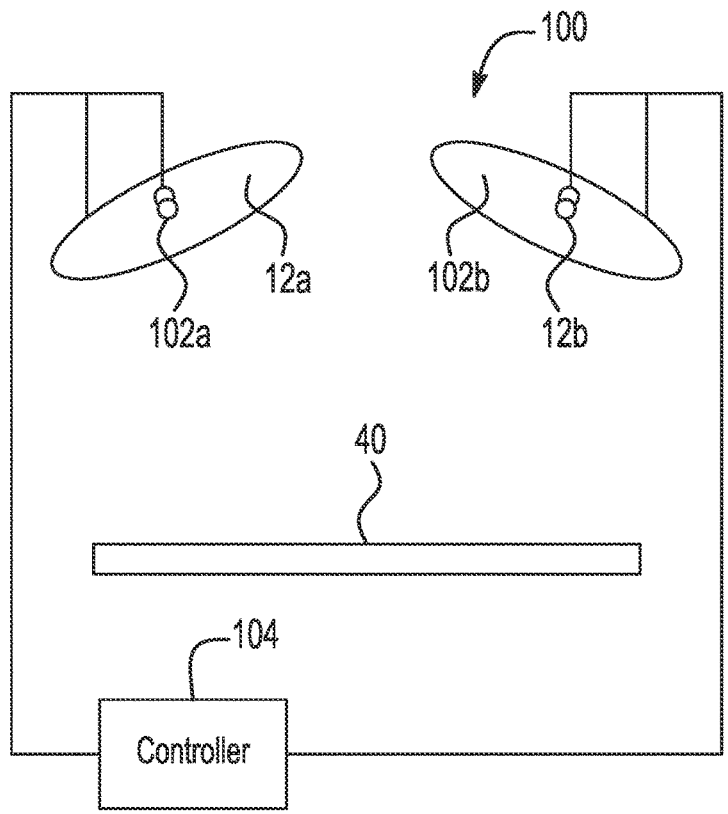
FIG. 8 is a block diagram illustrating an exemplary light system in accordance with the invention.

Moving to FIG. 8, illustrated is an exemplary light system 100 in accordance with the invention. The light system 100 include a plurality of lightheads, such as first light head 12a and second lighthead 12b previously described with respect to FIGS. 1 and 2. As will be appreciated, while the exemplary lightheads are part of a surgical lighting system, aspects of the invention are applicable to other types of lighting system and reference to a surgical lighting system is merely exemplary. At least one of the plurality of lightheads 12a, 12b includes a sensor 102a, 102b, the sensor operative to measure a characteristic of visible light (e.g., an intensity and/or a color of light). The sensors 102a, 102b, which are conventional light detection sensors known in the art, are configured such that they monitor a focal area 44a, 44b of the respective lighthead 12a, 12b on an object 40. Thus, sensor 102a monitors the focal area 44a of the first lighthead 12a, while sensor 102b monitors the focal area 44b of the second lighthead 12b. A controller 104 is communicatively coupled to the lightheads 12a, 12b and to the sensors 102a, 102b and operative to command the lightheads 12a, 12b to output light at a specific intensity, color, etc. with a fixed or varying characteristic. The controller 104 also receives from the sensors 102a, 102b a signal corresponding to a measured characteristic of light within the focal area 44a, 44b of the respective lighthead 12a, 12b. The controller 104 includes logic configured to carry out a method in accordance with the invention to detect a co-illumination state or independent state of operation and, if in the co-illumination state reduce light output to reduce exposure to light energy. Such logic may be in the form of a discrete circuit, an application-specific integrated circuit (ASIC), a processor and memory having instructions stored therein that are executable by the processor, or the like.

Figure 9:
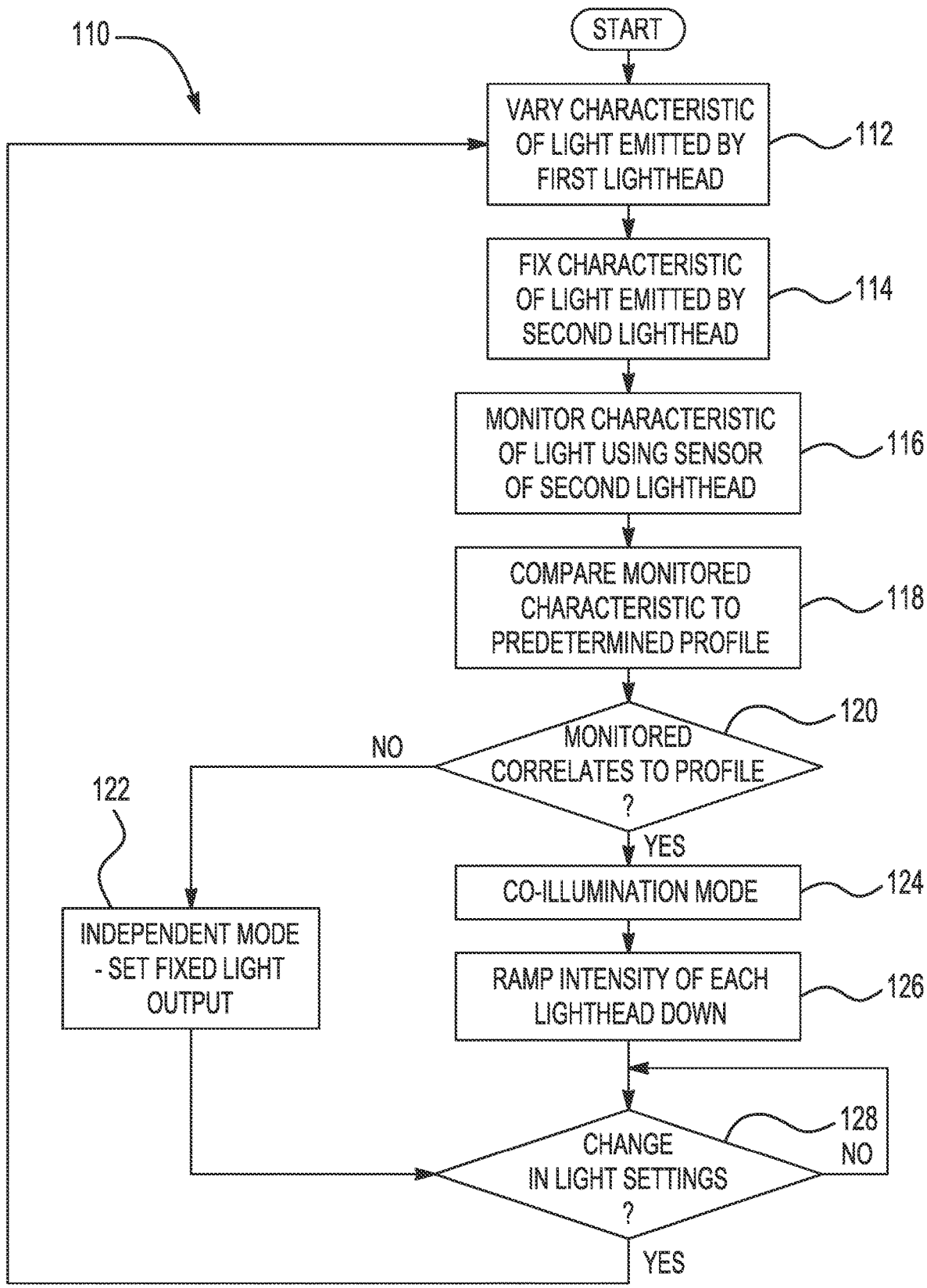
FIG. 9 is a flow chart illustrating exemplary steps of a method in accordance with the invention.

Referring now to FIG. 9, illustrated is a flow diagram that depicts an exemplary method 110 of using visible light emitted by the lightheads to determine co-illumination mode or independent mode of operation, and adjusting light output based on the determination. Although the method descriptions and flow chart may show specific orders of executing steps, the order of executing the steps may be changed relative to the order described. Also, two or more steps described in succession may be executed concurrently or with partial concurrence. One or more of the described or illustrated steps may be omitted.

The exemplary method of FIG. 9 may be implemented using coded instructions (e.g., computer readable instructions) stored on one or more non-transitory computer readable media such as flash memory, read-only memory (ROM), random-access memory (RAM), cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. Typical non-transitory computer readable media include electronic memory devices, magnetic memory devices and optical memory devices. The method may be executed by an electronic device, such as the controller 104. In one embodiment, to carry out the method, the logical instructions embodying the method are executed by a processor of the controller 104. Alternatively, the method may be at least partially implemented in hardware of the electronic device (e.g., a discrete circuit, an application-specific integrated circuit (ASIC) or the like).

Beginning at step 112, a characteristic of light emitted by a first lighthead 12a is varied in a manner that is imperceptible to the human eye. For example, the intensity of light output by the lighthead can slowly varied in an oscillating manner, where the period of oscillation is sufficiently long and/or the change in intensity is sufficiently small that the change is not perceivable. Alternatively or additionally, the color of the light may be slowly varied over time such that the variation is not perceivable (e.g., white light may be slowly varied over time between a warmer white light and a cooler white light). At step 114 the light output by a second lighthead 12b is set to have a fixed characteristic, e.g., the light emitted by the light head is fixed in intensity and/or does not vary in color. Next at step 116 the sensor associated with the lighthead having the fixed characteristic, i.e., the second lighthead 12b in the present example, monitors the focal area 44b for that lighthead (the second lighthead in the present example). If co-illumination is not occurring then the sensor 102b only sees the fixed characteristic of the lighthead 12b and generates sensor data that is fixed (non-varying). Conversely, if co-illumination is occurring then the sensor 102b will see light from both lightheads (i.e., a fixed light characteristic and a varying light characteristic) and generates sensor data that varies with respect to time.

Moving to step 118, the data provided by the sensor 102b has signal processing operations applied and the processed signal is compared to the light characteristic profile of the first lighthead 12a to determine if there is a correlation between the two by comparing the correlation coefficient to a predetermined threshold to establish co-illumination. For example, if the correlation coefficient exceeds a threshold then it can be said there is a correlation between the signals, and if the correlation coefficient is below the threshold then there is insufficient correlation between the signals. At step 120 if there is insufficient correlation between the signals then the method moves to step 122 and independent mode of operation is set for the lightheads 12a, 12b and the light output by each lighthead is set to a preset fixed value. The method then moves to step 128. Moving back to step 120, if it is determined there is a correlation between the signals, then the method moves to step 124 where co-illumination mode of operation is set for the lightheads 12a, 12b, and at step 126 the light intensity for each lighthead 12a, 12b is ramped down so as to reduce the total light energy exposure to patients and medical personnel. In one embodiment the reduced light level of the first and second lightheads is selected so that combined illuminance does not exceed the maximum for a single lighthead, about 160,000 lux. Alternatively, in another embodiment the reduced light level of the first and second lightheads is selected so that combined illuminance can exceed the maximum for a single lighthead by about 25%, about 200,000 lux. In yet another embodiment, the light level output by the first and/or second lighthead is adjusted to compensate for blockage, such as described in U.S. Pat. No. 10,271,398 and titled ADAPTIVE SHADOW CONTROL SYSTEM FOR A SURGICAL LIGHTING SYSTEM, the contents of which is hereby incorporated by reference in its entirety. The method then moves to step 128 to determine if a change in settings have occurred. Such settings can include pointing one or both lightheads in a different direction, or changing a distance of one or both lightheads from the object 40, detecting a substantial amount of blockage, a detected change in acceleration or angular rotation, or a user commanded increase in intensity. If no change is detected, the method loops at step 128, while if a change is detected the method moves back to step 112 and repeats.

Accordingly, co-illumination detection of multiple lightheads can be implemented using visible light and, thus, a secondary emission technology is not needed to detect such co-illumination. Further, based on detection of co-illumination, steps can be taken to reduce medical staff and patients from excessive exposure to light energy.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A method for operating a lighting system having a first lighthead and a second lighthead distinct from the first lighthead, the second lighthead having associated therewith a light sensor configured to detect an intensity of visible light incident on the target surface in the region where the second lighthead is focused, the method comprising:
 varying a characteristic of visible light emitted by the first lighthead according to a predefined profile;
 fixing a characteristic of visible light emitted by the second lighthead;
 detecting by the light sensor a characteristic of visible light incident on the target surface over a period of time;
 comparing the characteristic of the light detected by the light sensor over the period of time to the characteristic of light defined in the predetermined profile; and determining if the first and second lighthead are operating in a co-illumination state or an independent state based on the comparison.

2. The method according to claim 1, further comprising setting a mode of operation of the first and second lighthead based on the determined operating state.

3. The method according to claim 1, wherein setting comprises setting the mode of operation of the first and second lighthead to co-illumination mode when the comparison indicates the characteristic of the light detected by the light sensor is sufficiently well correlated with the characteristic of light defined by the predetermined profile.

4. The method according to claim 1, wherein setting comprises setting the mode of operation of the first and second lighthead to independent mode when the comparison indicates the characteristic of the light detected by the light sensor is substantially non-varying.

5. The method according to claim 1, further comprising upon setting co-illumination mode of operation, ramping an intensity of light emitted by the first and second lightheads down such that a combined light intensity produced by the first and second lightheads is at a predetermined intensity.

6. The method according to claim 1, wherein the predetermined profile comprises a characteristic of light that has a sinusoidal profile.

7. The method according to claim 1, wherein the predetermined profile has a characteristic of light that varies in frequency.

8. The method according to claim 6, wherein the predetermined profile has a frequency less than 1 Hertz.

9. The method according to claim 1, wherein the characteristic comprises an intensity of light.

10. The method according to claim 9, wherein the characteristic is an intensity of light, and varying includes varying a peak-to-peak intensity of light by about 30 percent relative to a nominal intensity.

11. A surgical lighting system, comprising:
a first lighthead configured to selectively emit a first visible light in a first direction;
a second lighthead distinct from the first lighthead, the second lighthead configured to selectively emit a second visible light in a second direction;
a sensor corresponding to the second lighthead and configured to sense visible light in a focal area of the second lighthead; and
a controller operatively coupled to the first lighthead, the second lighthead, and the sensor, the controller configured to
vary a characteristic of the first visible light over a period of time according to a predefined profile,
fix a characteristic of the second visible light over the period of time, and
compare a characteristic of the light detected by the light sensor over the predetermined time to a characteristic of light in the predetermined profile; and
determine if the first and second lighthead are operating in a co-illumination state or an independent state based on the comparison.

12. The surgical light according to claim 11, wherein the controller is configured to set a mode of operation of the first and second lighthead based on the determined operating state.

13. The surgical light according to claim 10, wherein the controller is configured to set the mode of operation of the first and second lighthead to co-illumination mode when the comparison indicates the characteristic of the light detected by the light sensor is sufficiently well correlated with the characteristic of light in the predetermined profile.

14. The surgical light according to claim 11, wherein the controller is configured to set the mode of operation of the first and second lighthead to independent mode when the comparison indicates the characteristic of the light detected by the light sensor is substantially non-varying.

15. The surgical light according to claim 11, wherein the controller, upon setting co-illumination mode, is configured to ramp an intensity of light emitted by the first and second lightheads down such that a combined light intensity produced by the first and second lightheads is at a predetermined intensity.

16. The surgical light according to claim 11, wherein the predetermined profile is a sinusoidal profile.

17. The surgical light according to claim 11, wherein the predetermined profile varies a frequency of a characteristic of the emitted light.

18. The surgical light according to claim 16, wherein a frequency of the predetermined profile is less than 1 Hertz.

19. The surgical light according to claim 11, wherein a peak-to-peak intensity of light set by the predetermined profile varies by up to about 30 percent relative to a nominal intensity.

* * * * *